(12) United States Patent
Papazolgou et al.

(10) Patent No.: US 6,524,336 B1
(45) Date of Patent: Feb. 25, 2003

(54) ENDOVASCULAR GRAFT

(75) Inventors: Konstantinos O. Papazolgou, Salonika (GR); Michael P. DeBruyne; John A DeFord, both of Bloomington, IN (US); Erik E. Rasmussen, Slagelse (DK)

(73) Assignees: Cook Incorporated, Bloomington, IN (US); William Cook, Europe A/S, Bjaeverskov (DK)

( * ) Notice: Subject to any disclaimer, the term of this patent is extended or adjusted under 35 U.S.C. 154(b) by 0 days.

(21) Appl. No.: 09/286,910

(22) Filed: Apr. 6, 1999

Related U.S. Application Data

(60) Provisional application No. 60/081,156, filed on Apr. 9, 1998.

(51) Int. Cl.[7] .................................................. A61F 2/06
(52) U.S. Cl. ...................................... 623/1.35; 623/1.16
(58) Field of Search ................................ 623/1.35, 1.1, 623/1.11, 1.27, 1.31, 1.13, 1.16

(56) References Cited

U.S. PATENT DOCUMENTS

| | | | | |
|---|---|---|---|---|
| 5,609,627 A | * | 3/1997 | Goicoechea et al. | 623/1.35 |
| 5,632,763 A | * | 5/1997 | Glastra | 623/1.35 |
| 5,632,772 A | * | 5/1997 | Alcime et al. | 623/1.35 |

* cited by examiner

*Primary Examiner*—David J Isabella
(74) *Attorney, Agent, or Firm*—Richard J. Godlewski

(57) ABSTRACT

Disclosed is a medical device graft arrangement comprising a main graft and at least one peripheral graft wherein the grafts are expandable. Upon insertion of the peripheral graft(s) into the main graft, the peripheral grafts expand and seal the junction of the graft arrangement to provide fluid communication between the lumens of the main and peripheral grafts. The graft arrangement optionally has a cover folded in such a manner to provide further sealing.

20 Claims, 13 Drawing Sheets

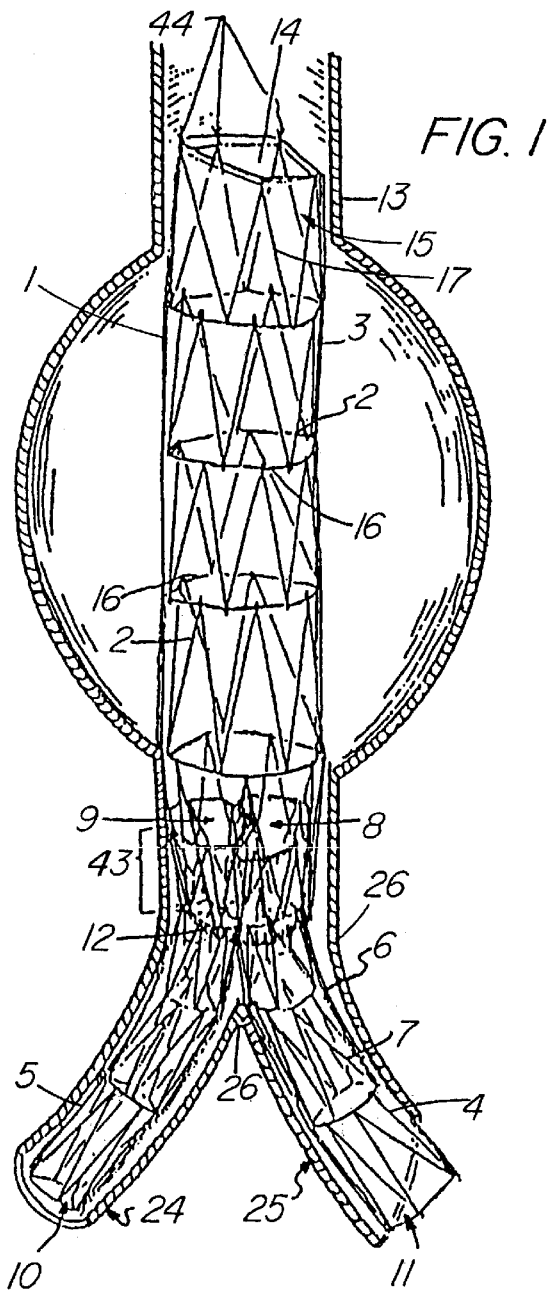
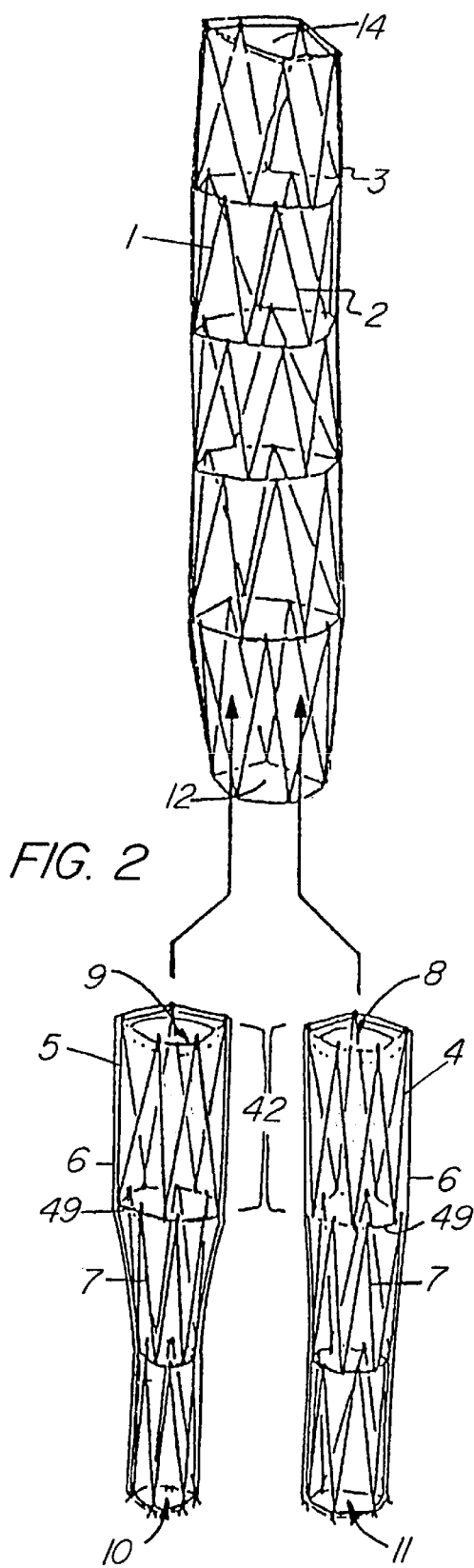
FIG. 1
FIG. 2

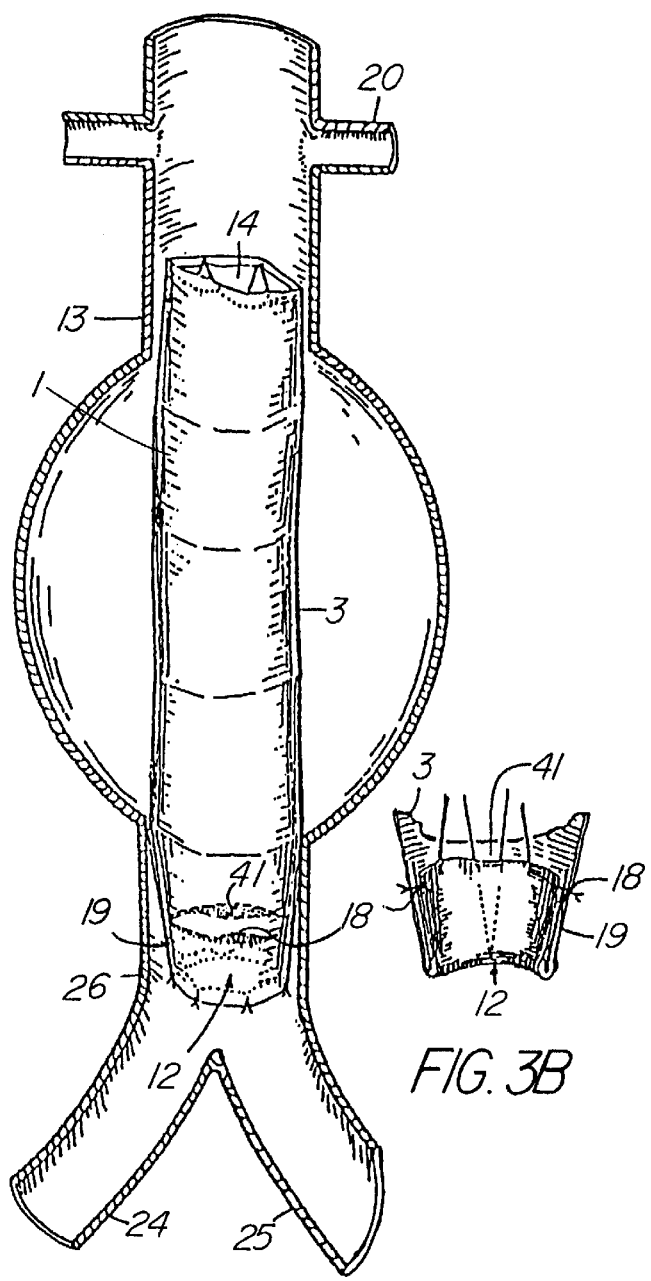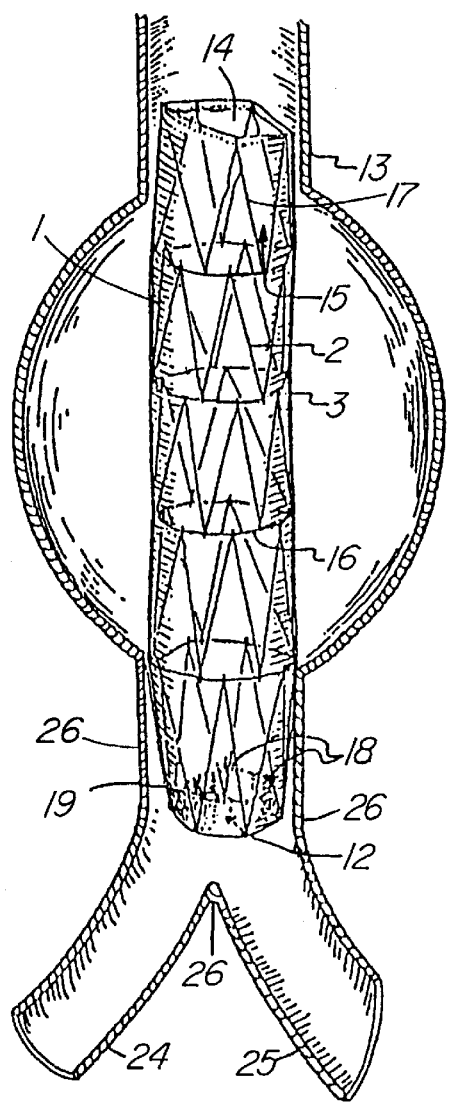
FIG. 3A
FIG. 3B
FIG. 3C

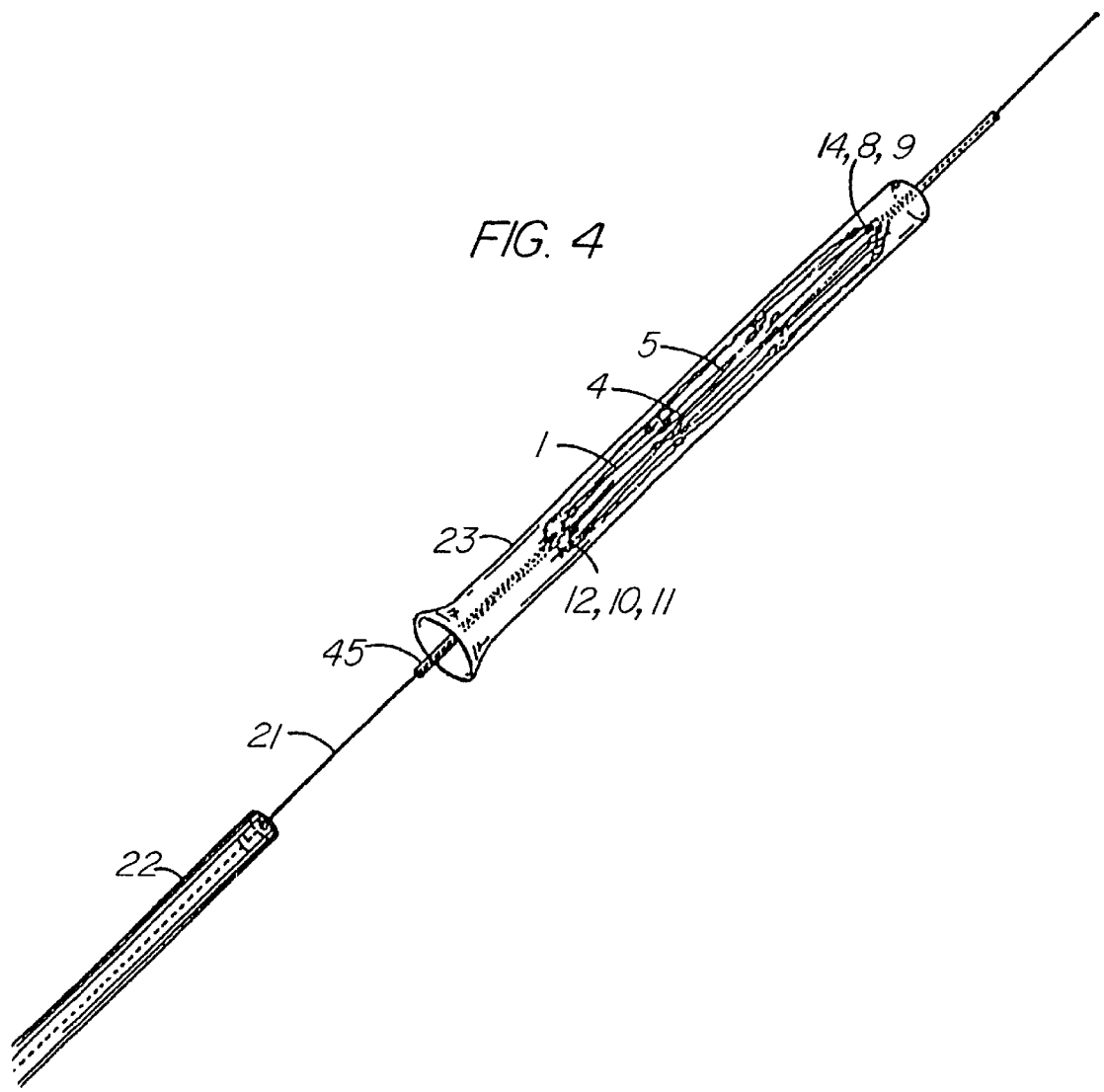

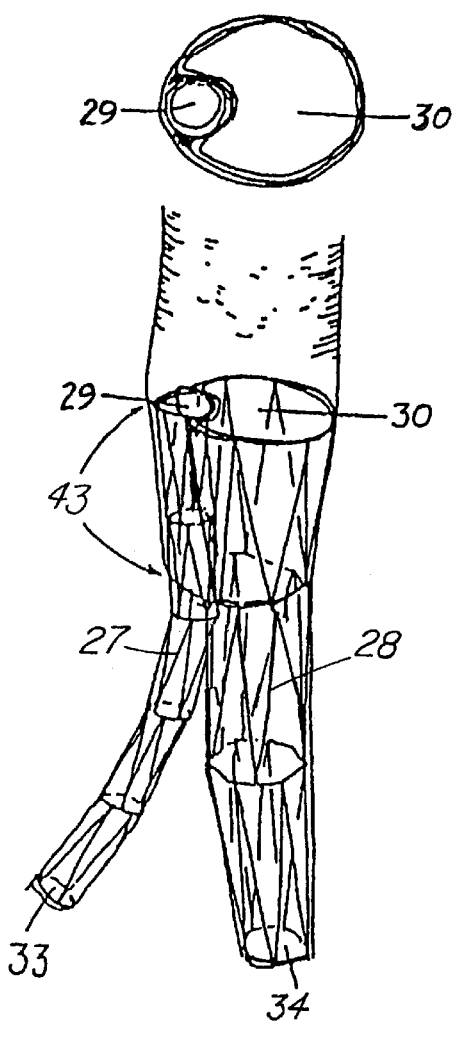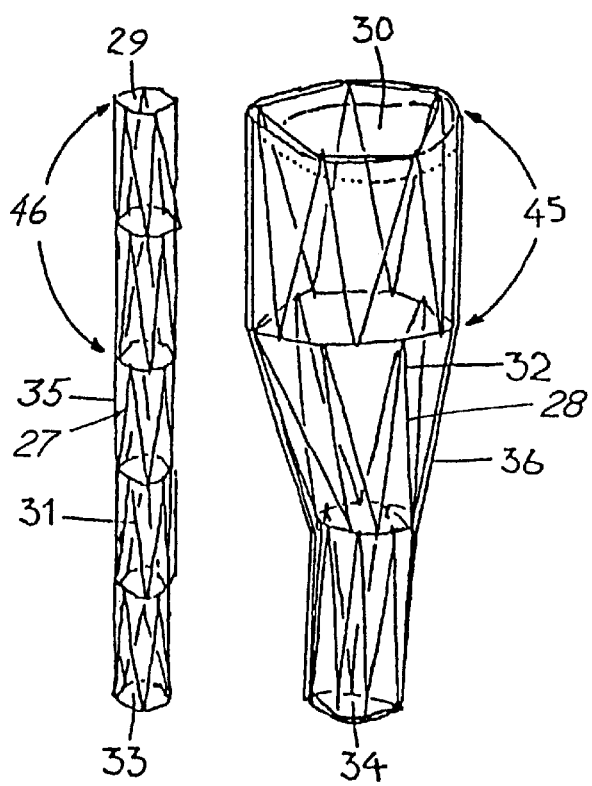
FIG. 6A
FIG. 6B

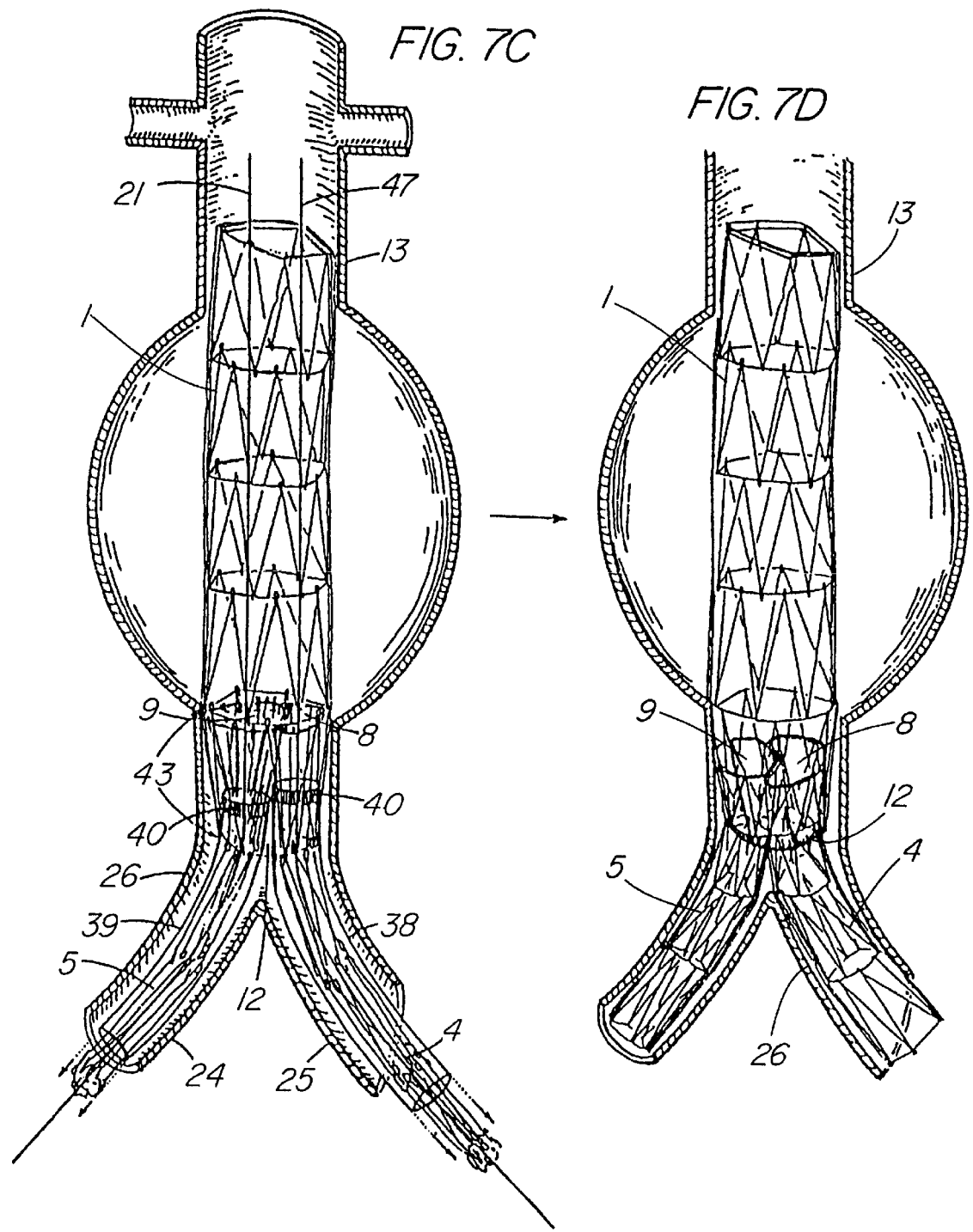

ENDOVASCULAR GRAFT

CROSS-REFERENCE TO RELATED APPLICATIONS

The application claims priority to provisional application Ser. No. 60/081,156, filed Apr. 9, 1998.

FIELD OF THE INVENTION

The present invention relates to medical devices and more particularly to grafts for repairing aneurysms.

BACKGROUND OF THE INVENTION

The endovascular approach to aneurysms of the abdominal aorta is a new technique for the therapy of aneurysms by the placement of grafts which are transferred to the position of placement by means of the vascular lumen from easily anatomically approachable regions, thus avoiding the need for open surgical operations. For the effective therapy of an aneurysm by this technique, it is necessary to have good circumferential application (contact) of the endovascular graft with the healthy, nondistended part of the blood vessel, so as to have complete exclusion of the distended arterial lumen by the pressure of the systemic arterial circulation, since the blood will now come out through the graft which substitutes for the vascular lumen. Furthermore, the endovascular graft must have a small initial diameter, which will allow its easy introduction and advancement from the entrance blood vessel to the position of placement, as well as its easy technical positioning. In abdominal aortic aneurysms there usually is a central neck region of the healthy blood vessel having a normal diameter underneath the renal vessels (at the point where the graft is surgically attached even by the classical operation). However, often the aortic distention is peripherally extended to the point of the aortic bifurcation at the two iliac arteries. This fact excludes the possibility of placing an endovascular tube graft due to the absence of a healthy peripheral contact point (neck). This often creates the necessity for the placement of endovascular grafts which can be attached to healthy regions of the iliac arteries more peripherally positioned to the distended aortic bifurcation with the simultaneous branching of the aortic blood flow to two cylinders of effluence. The systems that till now have been presented for the placement of aortic stent grafts are composed, first off, of a stent graft or of grafts comprised of two parts that are often complicated in their placement, have a large compressed size, and have imperfections in their support mechanisms and at their point of contact with the vascular wall. These result in the appearance of immediate or future complications or in the inability of placement for a sufficient number of circumstances.

Furthermore, it is a device that, when combined with the fact that it has a limited number of parts, can serve a large number of circumstances of different anatomical dimensions.

SUMMARY OF THE INVENTION

In one aspect of the invention, the graft arrangement comprises a main graft having a proximal end and a distal end, the main graft further having a proximal orifice to be located in and when expanded to be supported by a vascular vessel the main graft also having at least one distal orifice which when expanded serves to receive a proximal end of at least one expandable peripheral artery graft, wherein the main graft and the at least one expandable peripheral artery graft each comprises an expandable stent and at least one cover over and/or in the expandable stent; and wherein a cross-sectional area of one of the at least one distal orifice and the proximal end of a second at least one expandable peripheral artery graft, when expanded is sufficiently less than that second another cross-sectional area of the at least one distal orifice and the proximal end of the at least one expandable peripheral artery graft so as to form a seal between the grafts.

In another aspect, the distal end of the main graft has a part which is extended to form an iliac artery graft. Another part of the main graft has a distal opening or orifice which has a short inclined extension subtended in a distal direction so as to enable an iliac artery graft to be located therein when the short extension has been expanded. Such iliac artery graft has a proximal end which when expanded forms a seal with the short extension.

In another aspect, the distal end of the main graft has first and second or a pair of short extensions, one extension having the at least one distal orifice of the main graft, and the other extension having another distal orifice for the receipt of a respective iliac artery graft. Each of the iliac artery grafts will have a stent expandable to a cross-sectional area sufficiently greater than the cross-sectional area(s) of the distal orifices so that effective seals are formed.

In still another aspect, the graft arrangement includes an additional graft endovascularly inserted into the part of the aorta adjacent to the renal arteries, wherein the additional graft has, when expanded, a distal orifice region of cross-sectional area(s) less than that of the proximal orifice region so as to provide reinforcement and support for the proximal end of the main graft. The additional graft includes an expandable stent and at least one cover over and/or in the stent. Furthermore, the stent(s) of the additional part includes spikes, barbs, or hooks to facilitate securement to the part of the aorta adjacent to renal arteries. By way of example, the reinforcement is provided by folds in an internally folded cover to provide an increased fitness of cover material. The external cover has a proximal extension on the outer member of each seal whereby the extension is designed to be folded over the proximal end of the outer member and entering the proximal end of the internal member of each seal. As a result, such folded-over cover provides an extra sealing benefit.

The main graft can be selected to be of a length to extend from the said part to the bifurcation region where the aorta joins the iliac arteries. Alternatively, the main graft can be of a length such that it extends only across the said part. The part of the main graft in the region of the distal orifice is reinforced in order to support the iliac artery grafts when expanded. It is preferred for these stents to be self expanding. The cover at the distal end of the main graft preferably extends beyond the distal orifice so that after the iliac grafts have been inserted and expanded, the extension to the cover enters the interior of the iliac grafts and forms an extra seal therewith. The stent of the main graft can comprise spikes, hooks, or barbs designed to enter the wall of the said part in order to assist in the attachment of that graft to the said part.

BRIEF DESCRIPTION OF THE DRAWINGS

FIG. 1 is a schematic representation of the stent graft after its placement in the aneurysm of the abdominal aorta according to the present technique.

FIG. 2 is a schematic representation of the three parts of the central graft (main cylinder) and the two limbs (peripheral cylinders) from which are composed the stent graft according to the presented technique. The two limbs (peripheral cylinders) enter with their central region (of greater diameter) at the peripheral or distal region of the central cylinder and by their expansion create a leakproof branching of the central graft.

FIGS. 3A, 3B and 3C are representations of the analytical magnification of the central graft (main cylinder) which is placed in the abdominal aorta in the region between the out-branching of the kidney or renal arteries and the aortic bifurcation after its positioning and its expansion. In FIG. 3B, at the peripheral end can be discerned the refolding and attachment of the thin-walled external covering inside the main cylinder, to reinforce it and to make the branching of the main cylinder more leakage proof after the placement of the two peripheral cylinders.

FIG. 4 is a magnified representation of the cylinders in their compressed form inside the storage tubules which are small in diameter and equal to the diameter of the placement tubules inside the arteries as well as the propulsion device for the introduction and progression of the graft by means of a guide wire.

FIGS. 6A and 6B are a schematic representation of an alternative manner of construction of the limbs of the stent graft where the diameter of the central orifice at one of the limbs at the length of >2 cm (covered by the central cylindrical part) is equal to the diameter of the peripheral orifice of the main cylinder while the diameter of the other limb is smaller at the center of the orifice and part as well as at the cross-section of the central orifices after the expansion of the two limbs inside the central tube. If they were allowed to expand naturally, the cross-sectional areas of the combined limbs would be twice that of the distal, orifice or the central tube.

FIGS. 7C and 7D are shematic representation of the advancement of the two limbs inside the guide introduction tubules using the same technique as that for the placement of the central graft, and of their equal in height positioning by means of retraction of the introduction tubules when these are forwarded at an upright position which is at the same transverse level as the two limbs. FIG. 7D shows the complete release of the limbs (peripheral cylinders) along with the simultaneous or the nonsimultaneous withdrawal of the introduction tubules of both sides results in the fact that the expanded parts of the limbs will come in complete contact with the peripheral nonexpanded healthy region of the corresponding iliac blood vessel at which the flow of blood is directed.

DETAILED DESCRIPTION

Figure 5C:
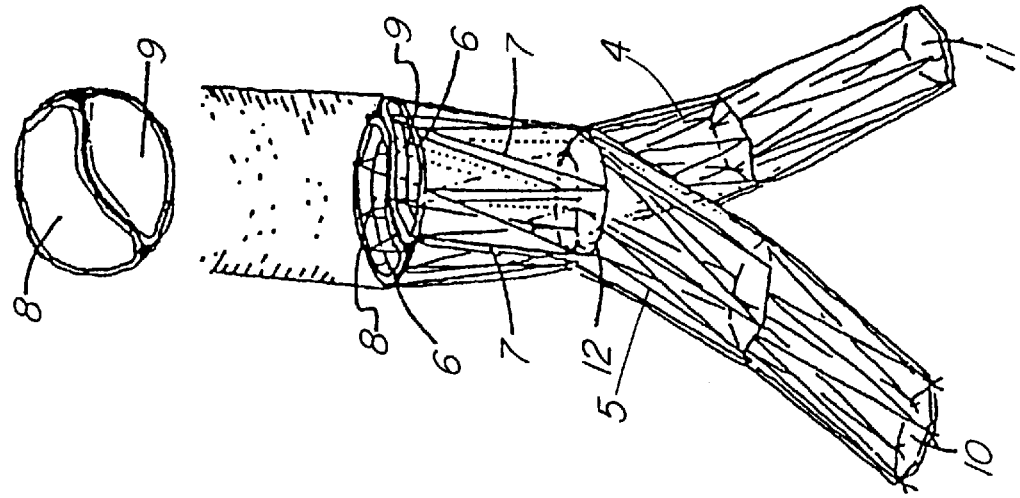
FIGS. 5A, 5B and 5C are three-dimensional schematic representation of the overlapping regions of the cylinder and of the two peripheral cylinders (limbs) after the expansion of the limbs inside the main cylinder and their leakage-proof application, not only amongst the limbs, but also with the central cylinder due to their self-expanding character. At the cross-section, one can clearly see the variety of shapes that the central orifices of the limbs can take when restricted at their external surface by the internal surface of the central cylinders at their overlapping parts.

In general, this device presents a stent graft for the therapy of abdominal aortic aneurysms without the need for the presence of healthy peripheral aortic walls, whereof the placement of one and only one graft tube would be possible. The need to avoid the pathological wall by airtightness in the nonexpanded part of the region of the iliac is accommodated by the branching of the central graft (main cylinder) at two peripheral tubes so that the blood can be driven toward both iliac arteries from the central aortic graft. Furthermore, the described graft should have the ability to be compressed to a small starting-off diameter, such that the advancement and placement in its compressed form is made possible by means of the small diameter inside the vascular lumen from distant regions (from the femoral artery to the abdominal aorta) which when released it can regain its original large diameter. This is accomplished in such a way so that it is able to achieve its leakproof perimetric contact with the internal surface of the healthy vascular lumen central and peripheral to an aneurysm. Until today, there have been proposed and used various devices for the accomplishment of the above goals. However, these are often complicated and difficult in their usage with the subsequent appearance of complications during and after the operation. To use these devices, it is necessary for those performing the operation to acquire lengthy experience and to have ample abilities. One aim of the device, which will be described as well as its technical positioning, is the simplification of the placement procedure, the minimization of the immediate and future complications and the enhancement of the percentage of successful clinical results with the goal of the possibility of a wide usage of the method of endovascular therapy of aneurysms for those patients where the placement of a stent-graft is necessary.

As shown in FIG. 1, the graft comprises a central main cylinder 1 of which the cylinder proximal end section 15 comes into contact with the internal surface of the healthy arterial wall of the aorta 13 at a level more central or proximal to the distended part of the aorta 13 and below the renal or kidney arteries 20 while the cylinder distal end 43 of the central main cylinder 1 sits upon the aortic bifurcation 26. The diameter or cross-sectional area of the cylinder proximal orifice 14 of the main cylinder 1 is equal to or larger than the aortal diameter of the healthy part of the aorta 13 on which the cylinder 1 will be placed. The diameter or cross-sectional area of the cylinder distal orifice 12 is constant and independent of whatever the aortic diameter happens to be at the level of its bifurcation 26 where the cylinder 1 will be placed. The length of the main cylinder 1 is determined by whatever happens to be the length between the central point of contact in the aorta 13 and its bifurcation 26.

The main cylinder 1 comprises a skeleton 2 which is preferably cylindrical, preferably metallic with a length that is substantially equal to the distance between the kidney or renal arteries 20 and the aortic bifurcation 26. The invention need not be metallic nor cylindrical though. This skeleton 2 has skeleton proximal predetermined diameter a and a compressed diameter β and comprises successive and serially connected cylindrical stents, such as Z shaped stents of variable length and with a Z configuration and comprising a biocompatible material, such as metal with memory, such as stainless steel wire or nitinol (a nickel titanium alloy with thermal memory). These Z stents may include the Gianturco type and are described in U.S. Pat. No. 4,580,568. The connection of these parts of the skeleton 2 can be accomplished either by sutures 16 that pass through the orifices of the last of the endcrests of each Z stent or by metallic joints (solderings) in such a manner so as to allow a certain amount of flexibility amongst the various Z stents of the skeleton 2 whilst the length of the skeleton 2 has as minimal as possible changes between its compressed diameter β and its skeleton proximal diameter α. However, other self-expanding skeletons with similar properties and characteristics which will possibly save the basic idea of the creation of the bifurcation of the herein presented stent-graft are also contemplated. The skeleton proximal end 17 may include a plurality of spikes, barbs or hooks which can, upon expansion and/or rotation penetrate the walls of aorta 13 for sealing and securement thereto.

The inner or outer surface of the main cylinder 1 is covered by an inner/outer surface tube 3 to form a graft which has a cylinder proximal orifice 14, and a cylinder distal orifice 12. The wall is preferably thin-walled and may comprise polytetrafluoroethylene (PTFE), DACRON(TM), polyurethane, or another type of biocompatible material. Alternatively, the inner and outer surfaces of the skeleton 2 can be covered by tubes, or it can be covered on its inner surface only by the surface tube 3. This surface tube 3 has a surface tube proximal diameter that is equal to that of the skeleton 2 and it has a surface tube distal orifice and a surface tube main body.

Figure 8:
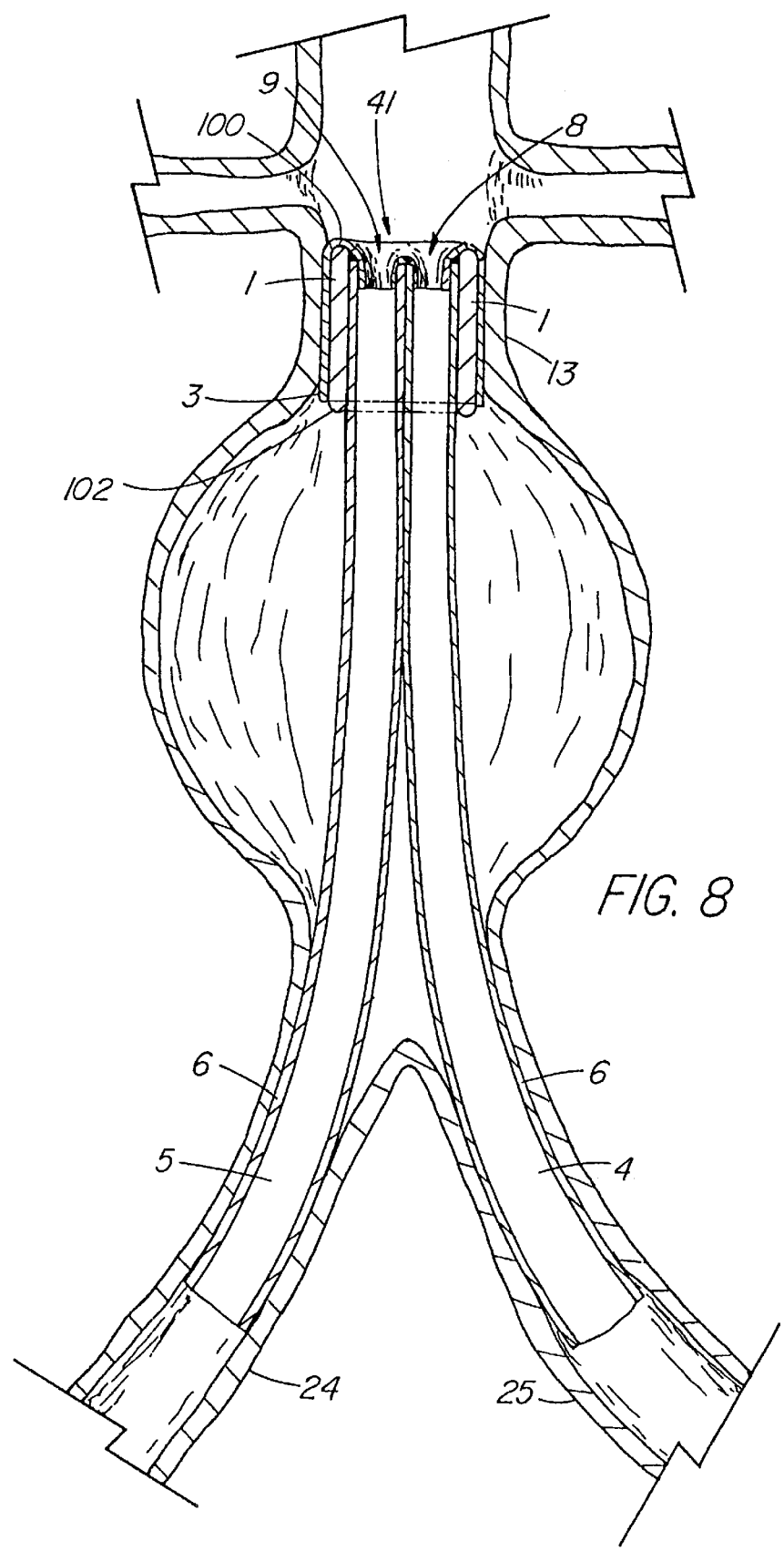
FIG. 8 illustrates an alternative arrangement in which the main graft is substantially contained within the region of the aorta containing the renal arteries. The distal end of the main graft is constructed in a manner similar to that in the other embodiments. The two limbs extend from the iliac arteries into the distal end of the main graft and are sealed in a similar manner.
Figure 10:
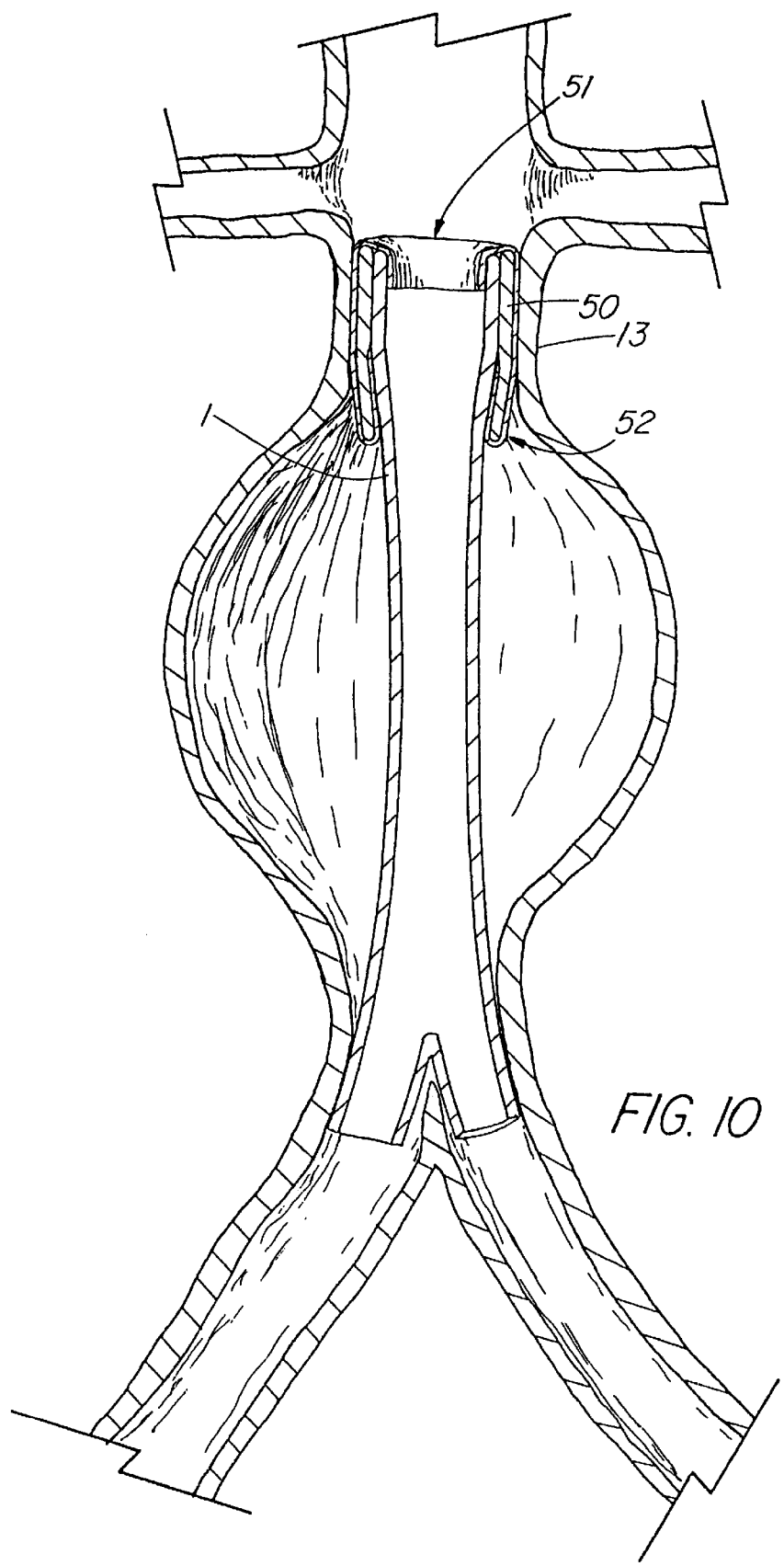
FIG. 10 illustrates a preferred alternative embodiment of the arrangement of FIG. 9 in which an additional engagement and sealing graft is provided at the proximal end thereof for seating the stent graft in the part of the aorta adjacent the renal arteries.
Figure 12:
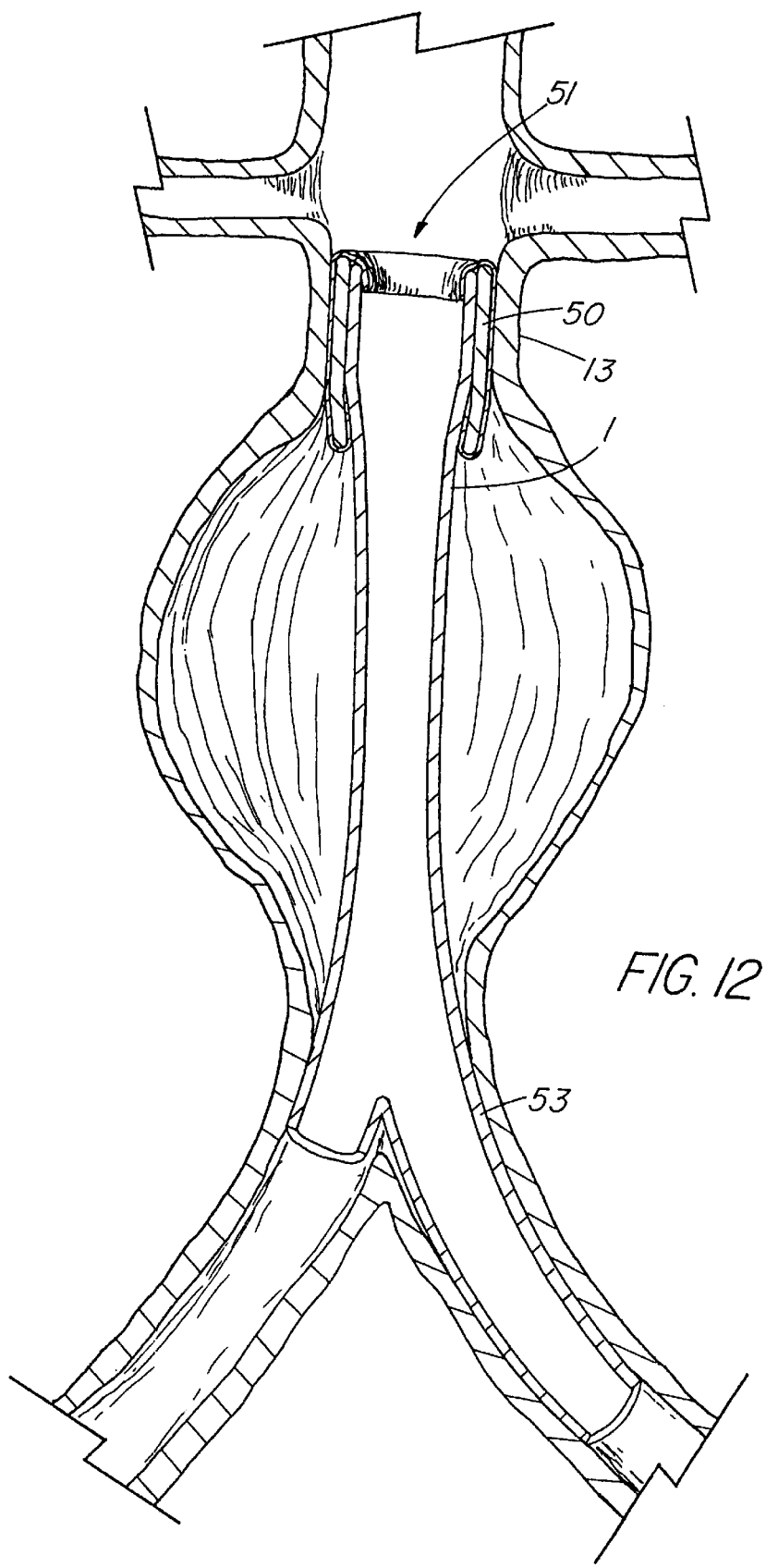
FIG. 12 illustrates still another alternative embodiment of the arrangement of FIG. 11 in which an additional engagement and sealing graft is positioned at the proximal end of the stent graft and the iliac graft has been affixed to the main graft.

With reference to FIGS. 1 and 2, the cylinder proximal orifice 14 has a diameter which is preferably substantially equal to or greater than that of the healthy part of the aorta 13 at the point of its contact with the main cylinder 1 more proximal to the aneurysm. The tube 3 of the graft is refolded (or may not be refolded) at the cylinder proximal orifice 14 of the skeleton 2 and is attached upon the cylinder proximal orifice 14 of the skeleton 2 by a series of connective sutures 44 at the end-crests of the skeleton proximal end 17. An outer covering can cover an outer enlargement at the cylinder proximal end 15 to firmly engage the walls of aorta 13 and then a flap can extend inwardly into the cylinder proximal orifice 14 to improve the seal, as shown in FIGS. 8, 10 and 12. The cylinder distal orifice 12 of the graft has a diameter of approximately 20–25 mm, and is refolded creating fold 18 of external cover 19 (see FIG. 3B) at a length of approximately 0.5–1.0 cm at the internal side of the cylinder distal orifice 12 of the skeleton 2 where it is internally attached by single sutures at two or at three different points of the skeleton 2. Thus, the flow of blood after the placement of the main cylinder 1 is accomplished inside the peripheral refolding of the graft of the main cylinder 1 at the cylinder distal 43 where the refolding creates two or three pockets (petals) 41 reducing the effective diameter of the opening of the cylinder distal orifice 12 of the main cylinder 1. Additional attachment points can be used, if desired, to establish additional petals 41.

Figure 7A:
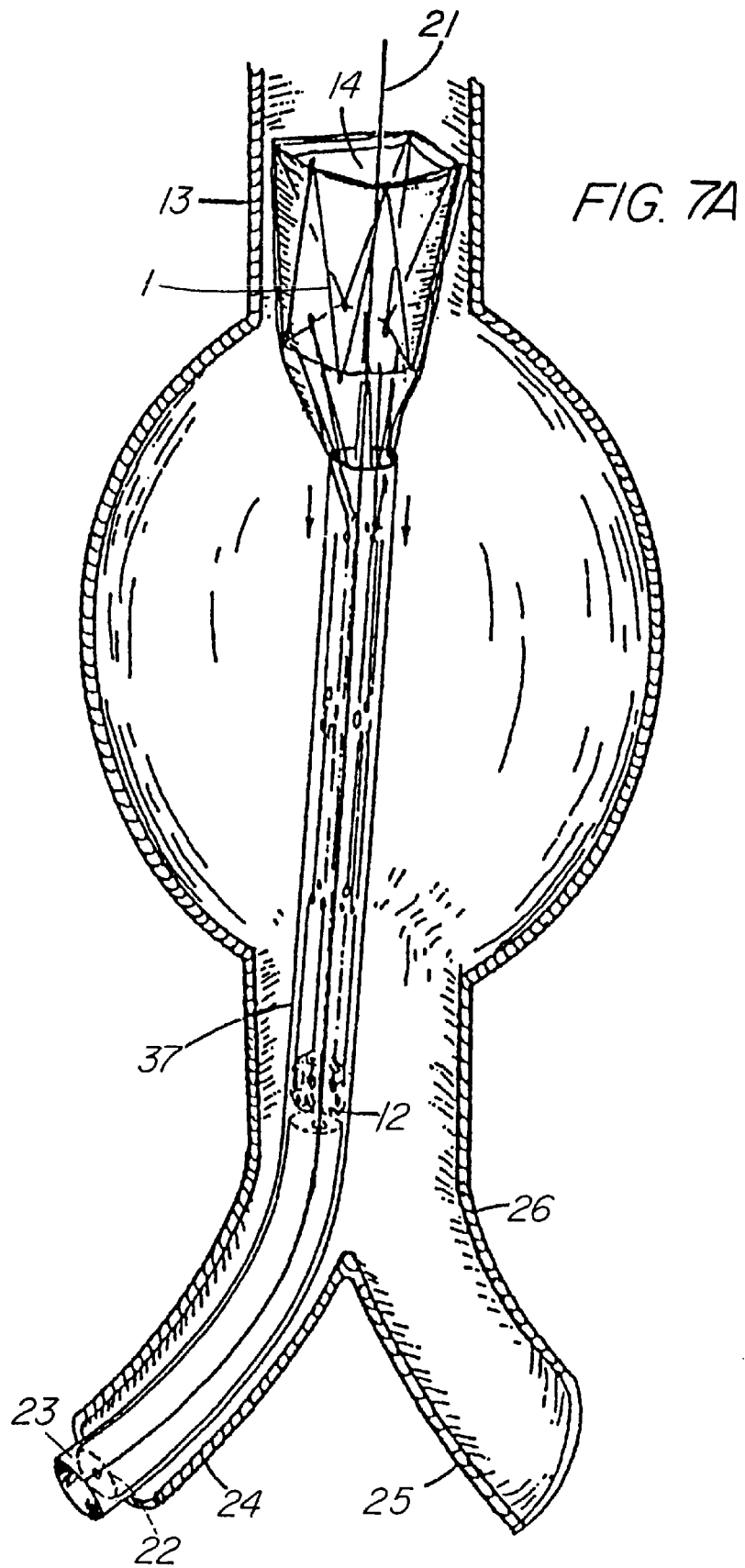
FIG. 7a is a schematic representation of the method of placement of the central graft (main cylinder). The central graft is found compressed inside the placement tubule where it is advanced since the guide wire passes through the graft and is brought to the point of placement with the help of the propulsion device and by the guide wire. The central orifice of the placement tubule has already been advanced more central to the aneurysm and when the graft reaches the position of placement, it is allowed to expand by means of maintaining the propulsion device stable and by means of the peripheral retraction of the placement tubule toward the propulsion device in such a manner so that during its expansion the graft will maintain its position unchanged.

With reference to FIGS. 3A–C, 4, and 7A, the main cylinder 1 has a starting-off diameter, which is equivalent to the outer surface tube 3 around the cylinder proximal orifice 14 and the cylinder distal orifice 12. The skeleton 2 expands the cylinder 1 to this diameter and to a compressed diameter much smaller than that of the original diameter in such a manner so that it can be compressed inside the storage tubule 23 which has a small diameter equal to that of the placement tubule 37 which is used for the advancement of the graft inside the blood vessels, particularly aorta 13 (FIG. 7A). During the compression of the main cylinder 1 inside the storage tubule 23, it has, at its center, a catheter 45 which is used for the insertion of the guide wire 21 (which after this it is removed) through the compressed inside of the storage tubule 23 and the main cylinder during the positioning process. The progression of the main cylinder 1 to the placement position is accomplished from its propulsion by the storage tubule 23 to the placement tubule 37, which as previously mentioned, has the same diameter. This is achieved with the help of a propulsion device 22 which moves upon the guide wire 21 which goes through the center of the main cylinder 1 and continues through the aneurysm.

Figure 5B:
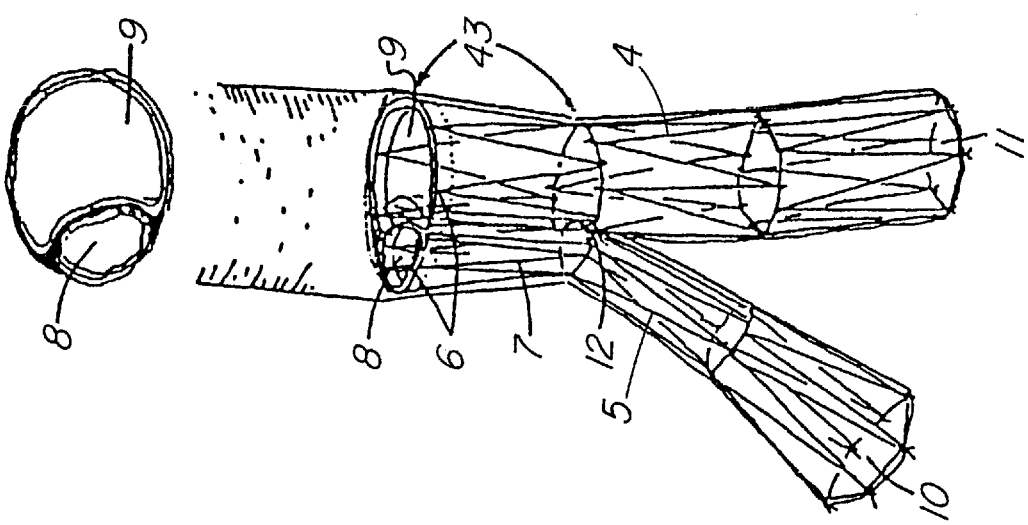
Figure 5A:
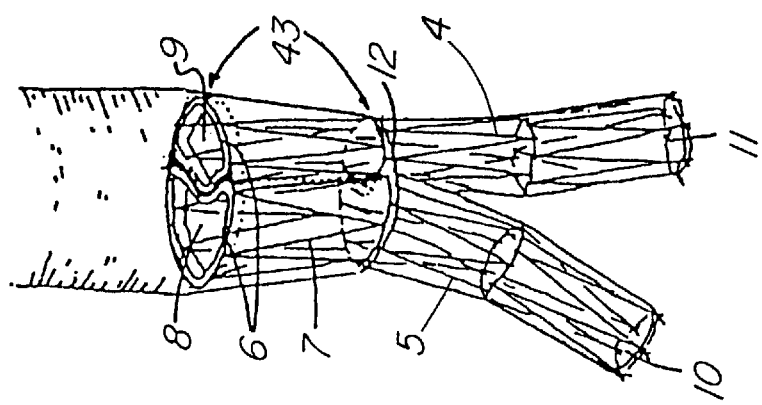

With respect to FIGS. 5A, 5B and 5C the stent-graft also comprises two peripheral cylinders 4, 5, which preferably are self-expanding stents or skeletons 7 identical to that of the main cylinder 1 but of different dimensions. Each skeleton 7 is covered at its external surface by an outer surface skeleton tube 6, which may have an identical or a different composition from that of the main cylinder 1 or that of outer surface tube 3, but are of different dimensions. Each peripheral cylinder has a peripheral cylinder proximal orifice 8, 9; a peripheral cylinder distal orifice 10, 11; a starting-off diameter; and a compressed diameter such that it becomes possible for each peripheral cylinder 4, 5 to be placed inside a storage tubule 23 (FIG. 4) exactly in the same way as with the main cylinder 1 but of a smaller diameter. The peripheral cylinder 4,5 can be advanced to the corresponding placement tubules 37, 38 (FIGS. 7A and 7B) inside of the blood vessels, such as the iliac arteries 24, 25. The outer surface skeleton tube 6 may cover the entire length of the peripheral skeleton 7 and is attached to the peripheral cylinder proximal orifice 8, 9 and the peripheral cylinder distal orifice 10, 11 of the peripheral skeleton 7 of each peripheral cylinder 4,5. Each peripheral skeleton 7 of the peripheral cylinder 4, 5 has a diameter in its expanded form equal to or greater than that of the outer surface skeleton tube 6 at each of its parts in such a manner so that it comes in complete contact at its external surface with the internal surface of the outer surface skeleton tube 6 that has a constant diameter at its expanded form and at each of its parts. The graft can be refolded to a small length, such as less than 5 mm, and does not have to, be refolded inside the peripheral cylinder proximal orifice 8, 9 of the skeleton of each peripheral cylinder and does not have to be refolded at the peripheral cylinder distal orifice 10, 11 of the skeleton of each peripheral cylinder where it is attached by sutures.

The diameter or diameters of the peripheral cylinder proximal orifices 8, 9 of each peripheral cylinders 4,5 is preferably equal to or approximately up to about 5 mm or more smaller in relation to the diameter of the cylinder distal orifice 12 of the main cylinder 1. Alternatively, each peripheral cylinder proximal orifice 8,9 can be equal to or greater than cylinder distal orifice 12, or each can be significantly smaller than orifice 12 by much more than 5 mm such as 10 or 20 mm. Experimentation of a simple nature can determine sizes of the peripheral cylinders 4,5 relative to cylinder distal orifice 12 in order to achieve a sealing affect between cylinders 1, 4 and 5.

With respect to FIG. 2 and FIGS. 5A and 7C, the diameter of the peripheral cylinder proximal orifice 8,9 of each peripheral cylinder 4,5 continues at a length of 2–2.5 cm at the central part 42 of the graft of each peripheral cylinder, which is the length of the first of the Z stents of the preferably self-expanding stents or skeletons 7 of each peripheral cylinder 4,5 and the point 49 where the first stent of the preferably self expanding skeleton 7 is connected to the second stent as has previously been mentioned. This central part 42 of each peripheral cylinder 4,5 is the part which enters into the cylinder distal end 43 of the main cylinder 1 for the creation of the stent bifurcation 32 of the main cylinder 1. The diameter of the peripheral cylinders 4,5, more distal to the previously mentioned central part 42, has a length and a diameter that vary according to the length and the diameter that is necessary so that the peripheral cylinder distal orifice 1 0, 11 of each of those two peripheral cylinders 4, 5 can come in complete contact with the healthy part of the corresponding iliac blood vessels 24, 25. That is to say, that the peripheral cylinder diameter and the length of each peripheral cylinder 4,5 can differ from each other (such as is seen in FIGS. 5B and 5C) in relation to the dimensions of the iliac blood vessels 24, 25 of their healthy part and of the length of the damage of each, from the bifurcation 26 of the aorta 13.

With respect to FIGS. 5B and 6B, alternatively, the diameter of the central proximal orifice of the central part of each peripheral cylinder 4,5 can differ in size. Specifically, the diameter of the central orifice 30 and of the central part 45 of one 28 of the peripheral cylinders which enters from the cylinder distal orifice 12 of the main cylinder 1, is equal to the diameter of the peripheral part and of the cylinder distal orifice 12 of the main cylinder 1, while the diameter of the central part 46 and the orifice 29 of the other peripheral cylinder 27 can be smaller to create a smaller compressed peripheral cylinder diameter and its progression inside of a smaller in diameter placement tubule, percutaneously. In this case, the expanding ability of the skeleton 31 of the smaller in diameter peripheral cylinder 4,5 is equal to or greater than that of the skeleton 32 of the peripheral cylinder with the greater central diameter. The length as well as the periphery of the distal orifice 33, 34 of each peripheral cylinder 27,28 can vary as previously mentioned according to the dimensions of the iliac blood vessels and their condition.

Again with respect to FIGS. 5B and 6B, the covering cylinder 35, 36 of the peripheral skeleton 31, 32 of the peripheral cylinders 27, 28, comprises a cylinder made out of thin-walled polytetrafluoroethylene (PTFE), DACRON (tm), or another type of biocompatible material. This thin-walled cylinder preferably has the previously mentioned constant dimensions of the peripheral cylinders 27,28 in its noncompressed form as well as after its expansion by the self-expanding main cylinder skeleton internally. The material of the thin-walled covering cylinder 35, 36 of the metallic skeleton of the peripheral cylinders 27,28 can cover the cylindrical metallic skeleton at its external surface or at its external and internal surfaces or at its internal surface.

Technical Placement—Creation of a Bifurcation

Figure 7B:
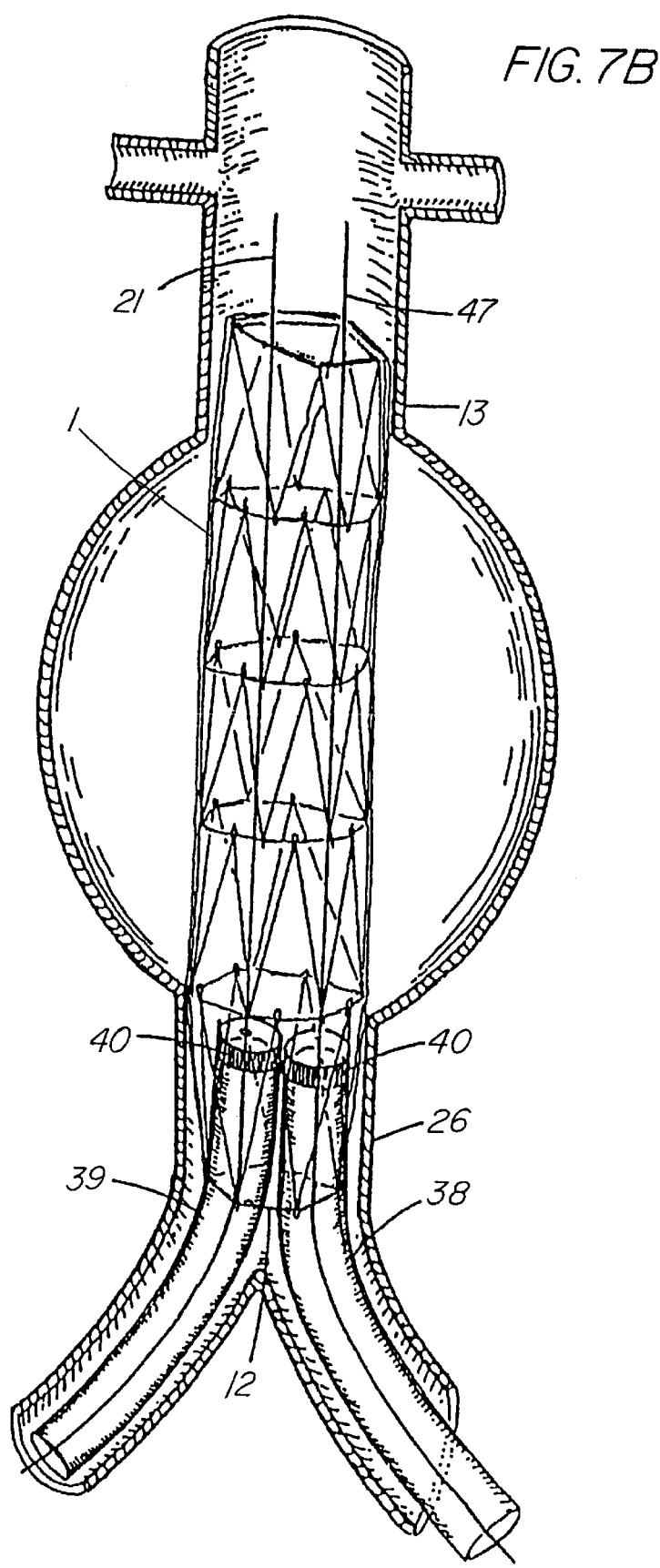
FIG. 7b is a schematic representation after the placement of the central graft wherein a second guide wire is advanced from the other iliac artery and by the peripheral orifice of the main cylinder. On the guide wires of both sides, the placement tubules are advanced by an X-ray shadowing ring at their central orifice, through the iliac arteries and through the peripheral orifice of the main cylinder inside the peripheral part of the main cylinder.

The herein presented stent-graft is created by the placement of three cylinders (1,4,5) (main and two peripheral) of which it is composed and which is executed in the following manner:

With respect to FIGS. 4, 7A and 7B, after the percutaneous placement of the guide wire 21 from the femoral artery and in a head on direction towards the aorta, an angiogram is performed so as to determine the height of the kidney arteries. At this point, as well as at the point of the aortic bifurcation, the X-ray shadowed guided position is monitored by X-rays. The introduction placement tubule 37, inside of which the main cylinder 1 will be advanced during its placement, is advanced with the guide wire 21. The introduction placement tubule 37 has at its central end an X-ray shadowed ring 40 and at its peripheral end it has a hemostatic valve 39. During its endovascular advancement, the introduction placement tubule 37 has inside of it a diastolic device which makes easier its percutaneous entrance into the artery. The introduction placement tubule 37 is advanced inside the aorta 13 so far in as necessary so that the X-ray shadowed ring 40 at its central end will be found at a more central level than that of the out-branching of the kidney arteries 20. Then, the diastolic device is removed from inside of the introduction placement tubule 37. On the guide wire 21 through the hemostatic valve, the storage tubule 23 is advanced, the storage tubule 23 having a diameter equal to that of the introduction placement tubule 37, the storage placement tubule 23 carrying inside its lumen the compressed main cylinder 1 of the stent graft, the main cylinder 1 having a length equal to that of the distance between the point of the out-branching of the kidney arteries 20 and the aortic bifurcation 26 and a diameter of the cylinder proximal orifice 14 (after its expansion) which is equal to or greater than that of the aorta 13 at the height of the central neck directly underneath the kidney arteries.

With respect to FIGS. 7a, 7b 7C and 7D, the main cylinder 1 is advanced from the storage tubule 23 to the introduction placement tubule 37 and through this to the placement point with the help of a propulsion device 22, which passes through the center of the compressed main cylinder 1. When the main cylinder 1 which displays an X-ray shadow in its entire length, is advanced inside the introduction placement tubule 37 between the guide points that have been placed at the out-branching of the kidney arteries 20 and the aortic bifurcation 26, the propulsion device 22 is maintained in a stable condition by its central end which restrains the cylinder distal orifice 12 of the main cylinder 1 at the height of the aortic bifurcation 26. The introduction tubule 37 is pulled by the propulsion device 22 in a distal direction in such a manner so that the main cylinder 1 is progressively released from the introduction placement tubule 22 for its entire length and will expand. When it comes into contact with the internal surface of aorta 13 directly beneath the kidney arteries 20, it will become more round whilst the cylinder distal orifice 12 sits upon the aortic bifurcation 26. In this way, the dislocation of the main cylinder becomes impossible due to the constant length of the main cylinder skeleton 2, which is supported by the aortic bifurcation 26.

Then and after the initially progression of the propulsion device 22 inside the introduction placement tubule 37, it is advanced on the guide wire 21 through the cylinder distal orifice 12 inside of the main cylinder 1 so that the X-ray shadowing ring 40 will be found approximately 2–2.5 cm more central to the cylinder distal orifice 12 of the main cylinder 1.

In the same way, one of the two peripheral cylinders 4,5 is advanced inside of the introduction placement tubule 37 through the hemostatic valve. In this manner, the peripheral cylinder proximal orifice 8,9 will reach the height of the X-ray shadowing ring 40 of the introduction placement tubule 37.

With respect to FIG. 7b, percutaneous advancement of the guide wire 47 is achieved from the femoral artery of the other side after its percutaneous insertion. The guide wire 47 is proximally directed with the help of a guide catheter through the iliac artery 24,25 and through the cylinder distal orifice 12 of the main cylinder 1, which sits upon the aortic bifurcation 26 inside the lumen of the main cylinder 1. Advanced on, the guide wire 47 follows the second introduction placement tubule 38 with a diastolic device inside of it and an X-ray shadowing ring 40 at its central orifice. The second introduction tubule 38 is centripetally advanced through the cylinder distal orifice 12 and up to the point where the X-ray shadowing ring 40 at its central orifice is found at the same height, approximately 2–2.5 cm from the cylinder distal orifice 12 inside the main cylinder, with the X-ray shadowing ring 40 of the main orifice of the introduction placement tubule 38 of the other iliac artery inside of which is already found the peripheral cylinder 4, 5 of the other iliac artery its compressed form. Inside the second introduction placement tubule 38 end with the technique which was previously mentioned, the second peripheral cylinder 4,5 is advanced until the point where its central compressed end is at an equal height as that of the X-ray shadowing ring 40 of the second introduction placement tubule 38 inside of which it is advanced as well as with the central end of the compressed peripheral cylinder 4, 5 of the other side.

After they are X-ray monitored, the two compressed peripheral cylinders 4,5 inside of the introduction placement tubules 37, 38 have a position of equal height, both with their central ends, approximately 2–2.5 cm more central and inside of the cylinder distal orifice 12 of the main cylinder; that is to say, at the point of the union (joint) of the first with the second Z stent of their metallic skeleton which has a corresponding length, the introduction placement tubules 37, 38 are withdrawn simultaneously or nonsimultaneous in a centrifugal or distal direction and the peripheral cylinders are expanded according to the technique which was mentioned previously for the main cylinder as seen in FIG. 7D.

With respect to FIGS. 5A to 5C, after the expansion, the two peripheral cylinders 4,5, these having a self-expanding skeleton, preferably each with an equal strength of expansion at the end covered by their main cylinder part extended, are compressed due to the greater total diameter of both in relation to the diameter of the peripheral part of the central cylinder by the main cylinder. In this way, they come into leak-proof contact with the internal surface of the wall of the central cylinder, but also between them, however, maintaining the diameter of both peripheral cylinder orifices 8, 9 equal to the diameter of the distal end 43 of cylinder 1. The shape of the peripheral cylinder proximal orifices 8,9 of the two peripheral cylinders 4,5 can vary, without these, however, coinciding completely due to the equivalent expansive ability of their metallic skeletons, as is shown in FIGS. 5A, 5B, and 5C.

With respect to FIG. 3B, furthermore, the reversal of the main cylinder external cover 19 at the cylinder distal orifice 12 creates an additional valve mechanism at this level which hinders the escape of blood from the microchasms which may occur during the contact amongst the two distal cylinders, but also with the internal surface of the peripheral part 43 of the main cylinder.

In this manner, a blood leak-proof (without the escape of blood) bifurcation of the main cylinder 1 is created at the two peripheral cylinders 4,5 with peripheral cylinder proximal orifice 8,9 of variable shape and area.

The peripheral part of each peripheral cylinder 4,5 has a length and a diameter of the peripheral cylinder distal orifice 10, 11 that is analogous to those of the corresponding iliac artery 24, 25, so that after its expansion, it will come in complete contact with the internal surface of the healthy part of the wall of the iliac artery 24, 25.

After the placement of the graft, according to the manner which was previously mentioned, the direction of the flow of blood is achieved inside of the graft from the height of the kidney arteries 20 through the orifice of the two limbs and more peripheral to these inside of the iliac arteries with the simultaneous exclusion of the systemic arterial pressure and the blood circulation of the pathologically distended wall of the aneurysm of the aorta 13 which also includes the aortic bifurcation 26.

In another exemplary embodiment shown in FIG. 8, the graft arrangement comprises a main graft 1 which is formed in a manner similar to graft 1 of the other embodiments. It comprises an inner stent and an outer covering 3, the latter extending upward to form a flap 100 which when the assembly is operational, folds into the graft limbs to assist the sealing process.

The main graft 1 is introduced into aorta 13 with the cylinder proximal end 15,51 of the graft adjacent to the renal arteries 20 and with the cylinder distal end 102 of the graft adjacent to the distal end of aorta 13 to where the aorta 13 begins to flare out to form the proximal portion of the aneurysm. The graft is expandable to form a force fit within aorta 13. If desired the graft 1 can be provided with spikes, barbs, hooks, or other means to secure, which upon expansion of graft 1, rotate and embed themselves into the aorta 13 wall. The graft 1 has an internal cross-sectional area of at least cylinder distal end 102, much less than the sum of the external cross-sectional areas of the outer surface skeleton tube 6 of the peripheral cylinders 4,5. The latter are introduced via their respective iliac arteries 24, 25 in a tube such as placement tubule 37 and allowed to expand and for the seals with the main cylinder 1 and using the flap 100 of the cover extending beyond the provisional end of the cylinder 1. The latter is quite stable since it is supported by the firm or undiseased wall portion of the aorta 13 and its position is quite fixed. The round flap can have a plurality of slits at appropriate positions to facilitate entry into the two respective tubes.

Figure 9:
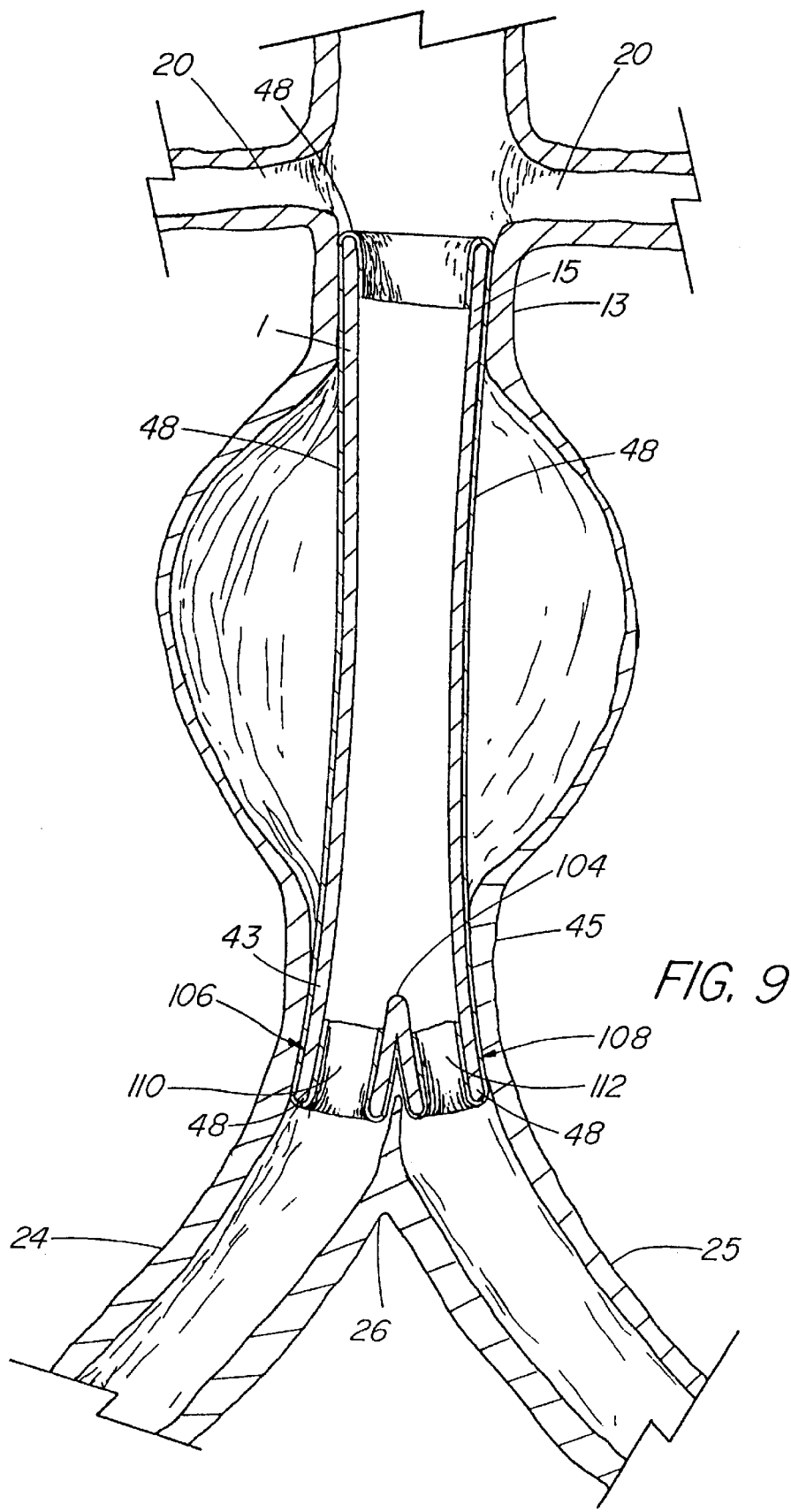
FIG. 9 illustrates another preferred alternative embodiment of the arrangement in which the bifurcated section thereof includes first and second or a pair of orifices in the form of short tubular receiving sections for receiving a respective iliac artery graft and which are to be sealed therewith.

In another exemplary embodiment shown in FIG. 9, a main graft 1 extends from the aorta 13 containing the renal arteries 20 to its cylinder distal end 43 in the region of the aortal bifurcation 26 of the iliac arteries 24, 25 with the lower end of the aorta. The cylinder distal end 43 contains a main cylinder bifurcated section 104 with two main cylinder bifurcated orifices 106, 108 in the form of short tubular receiving sections 110, 112 each for receiving a respective iliac artery graft, and to be sealed therewith.

Each graft contains an expandable stent which is preferably self expandable, but which can be expandable by other means, such as an inflatable balloon. Each stent is preferably made of stainless steel or nitinol which is self expandable, and has at least one cover 48 over and/or in the stent. The outer cover 48 on the receiving sections 110, 112 extends past the distal ends of these sections and extends in a proximal direction inside these sections. When each iliac graft is inserted into a respective section, the proximal end of the bent over cover 48 enters the proximal end of the respective iliac graft and thereby forms an additional seal.

The cross-sectional area of the proximal end of each iliac graft, when expanded is sufficiently greater than the cross-sectional area of the associated receiving section, so that when the iliac graft is in position in the section and expanded, it exerts an outward force against the sections to form a seal therewith. The proximal end of the iliac graft is of a shape similar to that of the respective receiving section and this enables an efficient seal to be achieved. The fold-over onto the cover 48 provides an additional seal.

Each receiving section 110, 112 is prefabricated with a special shape and with reinforcement to cope with the outward force exerted by the proximal end of the respective iliac graft. One preferred, but not exclusive form of reinforcement is achieved by a folding over of an inner cover, and the section preferably has an inwardly-shaped orifice at the distal end of the section to provide an extra clamping effect with the iliac graft.

The cylinder proximal end 15, of the main graft can have a bent over section of the outer cover 48 to provide an additional seal against aorta 13. The stent at the cylinder proximal end 15, of the main graft can have hooks or barbs to clamp onto the aortal wall 13, such barbs rotating into an outward engaging direction upon expansion of the stent in a known manner.

In FIG. 10, another alternative engagement and sealing graft arrangement is shown in which an additional relatively short graft 50 is provided by percutaneous iliac insertion to seal in the aorta 13. Graft 50 can be longer or shorter than the aorta 13 between the renal arteries and the aneurysm and is provided to add extra strength to the seal between the main graft proximal end 51 and the aorta 13. The graft 50 has a stent and preferably an extended cover 48 (not shown) to provide the extra sealing effect, and barbs for adhesion to the aortal wall 13. The main graft distal end 52 has a reduced cross-sectional area, as shown, and has folded-over covers to provide extra strength. Clearly, other forms of reinforcement of the graft 50 can be provided. In the exemplary embodiments shown in FIGS. 9 and 10, the iliac grafts can be percutaneously introduced into the expanded orifice sections when the iliac grafts are compressed as described previously. Upon expansion, an efficient, seal with folded-over cover 48 is achieved and the procedure is relatively simple compared to prior known procedures.

Figure 11:
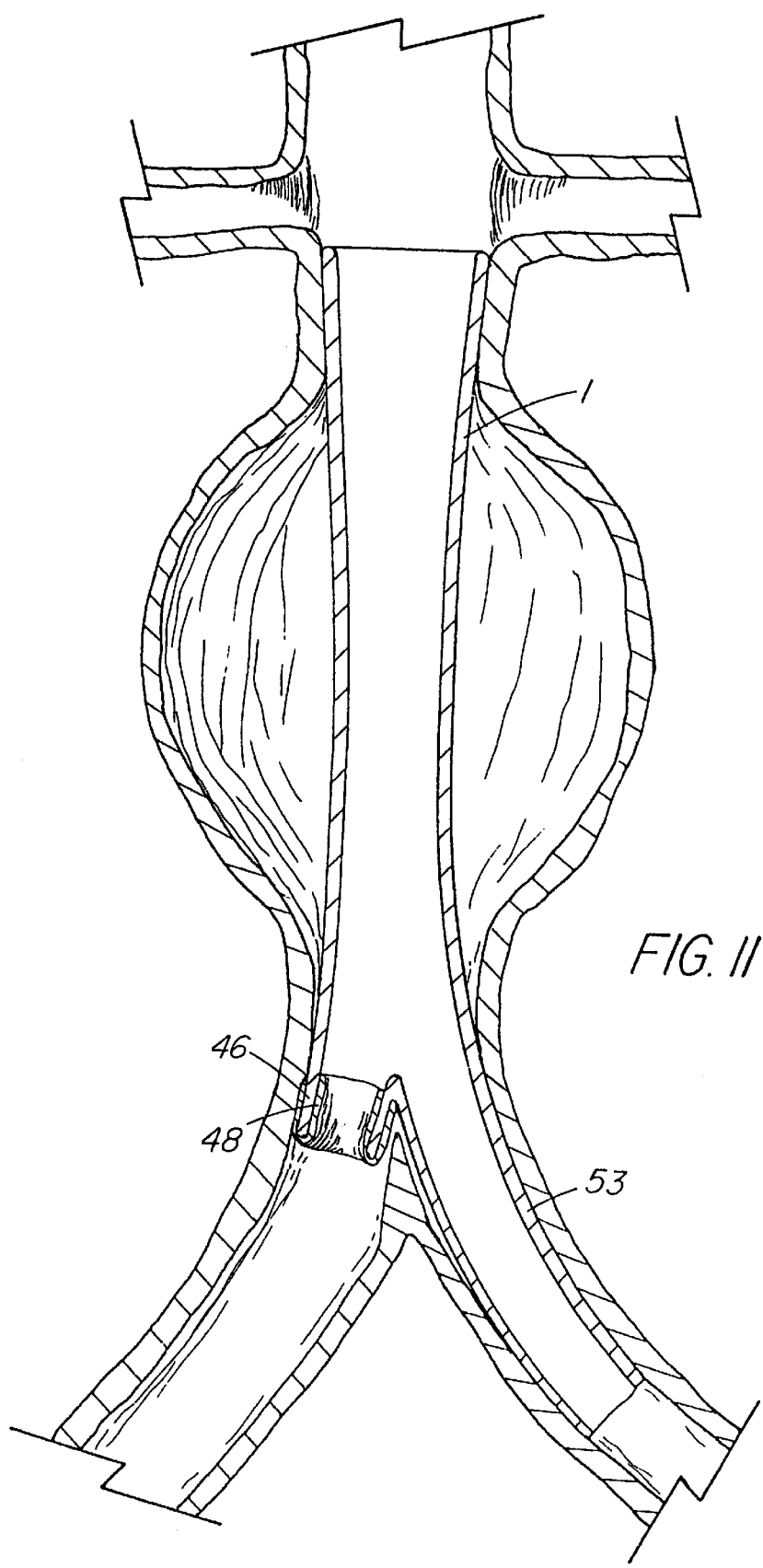
FIG. 11 illustrates yet another alternative embodiment of the arrangement similar to that of FIG. 9 in which a prefabricated iliac graft of the correct length and diameter has been affixed to the main graft.

With respect to FIG. 11, it shows an arrangement similar to FIG. 9 except that a prefabricated iliac graft portion 53 of correct selected length and diameter is fixed to the main graft 1. The prefabricated, iliac graft portion 53 replaces the receiving section 112 of FIG. 9, and is automatically sealed to the iliac artery at an appropriated distal position in that artery. This embodiment has the advantage of reducing the procedure time. The main graft 1 with iliac graft portion 53 thereon 53 is constructed and installed in the same manner as the graft 1 shown in FIG. 9. A cover flap 48 is preferably provided at the proximal end and at the receiving section 46.

The embodiment shown in FIG. 12 is the same as that shown in FIG. 11 except that the additional graft 50 of the FIG. 10 arrangement has been included. Parts 50, 51 and aorta 13 cooperate in the same way as previously described.

In the above described embodiments, self-expanding stents have been employed. If that is not desirable for any reason, then non-self expanding stents can be employed, but that would necessitate the use of expansion means such as balloons, such as those employed in angioplasty procedures.

Furthermore, the arrangement may be used in other vessels, tubes, or channels where a main graft and at least one peripheral graft is required, for example, in trachea-bronchi arrangements.

Those skilled in the art will know or appreciate using no more than routine experimentation, many equivalents to the specific embodiments of the invention described herein. These and all other equivalents are intended to be encompassed by the invention, the scope of which is defined by the appended claims.

What is claimed is:

1. A graft arrangement, comprising:
   a main graft having a proximal end and a distal end, the main graft further having a proximal orifice at the proximal end to be located in and when expanded to be supported by a vascular vessel;
   at least one expandable peripheral artery graft;
   the main graft also having at least one distal orifice at the distal end which when expanded serves to receive a proximal end of at least one expandable peripheral artery graft,
   wherein the main graft and the at least one expandable peripheral artery graft each comprises an expandable stent and at least one cover over and/or in the expandable stent; and
   wherein a cross-sectional area of the distal orifice when expanded is sufficiently less than that of the proximal end of the at least one expandable peripheral artery graft when expanded within the distal orifice so as to form a seal between the grafts.

2. The graft according to claim 1, wherein the distal end of the main graft has a part which is extended to form a peripheral artery graft, and another part which has a distal orifice which has a relatively short inclined extension subtended in a distal direction so as to enable the peripheral artery graft to be located therein when the short extension has been expanded, the peripheral artery graft having a proximal end which when expanded will form a seal with the short extension.

3. The graft according to claim 1, wherein the distal end of the main graft has first and second short extensions, the first extension having the at least one distal orifice and the second extension having another distal orifice for the receipt of the at least one peripheral artery graft, each of which will have a stent expandable to a cross-sectional area sufficiently greater than the cross-sectional area(s) of the distal orifices so that effective seals are formed.

4. The graft according to claim 1, further comprising an additional graft inserted into the vascular vessel, wherein the additional graft has, when expanded, a distal orifice region of cross-sectional area(s) less than that of the proximal orifice region so as to provide reinforcement and support for the proximal end of the main graft, the additional graft comprising an expandable stent and at least one cover over and/or in the stent.

5. The graft according to claim 2, further comprising an additional graft inserted into the vascular vessel, wherein the additional graft has, when expanded, a distal orifice region of cross-sectional area(s) less than that of the proximal orifice region so as to provide reinforcement and support for the proximal end of the main graft, the additional graft comprising an expandable stent, and at least one cover over and/or in the stent.

6. The graft according to claim 3, further comprising an additional graft inserted into the vascular vessel, wherein the additional graft has, when expanded, a distal orifice region of cross-sectional area(s) less than that of the proximal orifice region so as to provide reinforcement and support for the proximal end of the main graft, the additional graft comprising an expandable stent, and at least one cover over and/or in the stent.

7. The graft according to claim 4, wherein the stent(s) of the additional graft is (are) supplied with spikes, barbs, or hooks to facilitate securement to the vascular vessel.

8. The graft according to claim 5, wherein the stent(s) of the additional graft is (are) supplied with spikes, barbs, or hooks to facilitate securement to the vascular vessel.

9. The graft according to claim 6, wherein the stent(s) of the additional graft is supplied with spikes, barbs, or hooks to facilitate securement to the vascular vessel.

10. The graft according to claim 4, wherein the reinforcement is provided by folds in an internally folded cover to provide an increased thickness of cover material.

11. The graft according to claim 5, wherein the reinforcement is provided by folds in an internally folded cover to provide an increased thickness of cover material.

12. The graft according to claim 6, wherein the reinforcement is provided by folds in an internally folded cover to provide an increased thickness of cover material.

13. The graft according to claim 4, wherein an external cover has a proximal extension on an outer member of each seal whereby the extension is folded over a proximal end of the outer member and entering the proximal end of an internal member of each seal, such folded over cover providing an extra sealing facility.

14. The graft according to claim 5, wherein an external cover has a proximal extension on an outer member of each seal whereby the extension is folded over a proximal end of the outer member and entering the proximal end of an internal member of each seal, such folded over cover providing an extra sealing facility.

15. The graft according to claim 6, wherein an external cover has a proximal extension on an outer member of each seal whereby the extension is folded over a proximal end of the outer member and entering the proximal end of an internal member of each seal, such folded over cover providing an extra sealing facility.

16. The graft according to claim 7, wherein an external cover has a proximal extension on an outer member of each seal whereby the extension is designed folded over a proximal end of the outer member and entering the proximal end of an internal member of each seal, such folded over cover providing an extra sealing facility.

17. A graft arrangement, comprising:
 a) a main graft, the main graft being expandable and having a proximal orifice;
 b) first and second expandable peripheral artery grafts;
 c) the main graft also having a distal orifice end that when expanded receives at least one proximal end of the first and second expandable peripheral grafts;
 d) wherein each graft comprises an expandable stent and at least one cover over and/or in the stent; and
 e) wherein a cross-sectional area of the distal orifice when expanded is sufficiently less than the sum of a cross-sectional areas of the proximal ends of the peripheral grafts when expanded within the distal orifice, so as to form a seal with the distal orifice when the at least one peripheral graft is expanded therein.

18. The graft of claim 17 wherein the main graft further comprises an expandable stent.

19. The graft of claim 18 wherein the at least one peripheral graft further comprises an expandable stent.

20. A graft arrangement, comprising:
 a main graft, the main graft being expandable and having a proximal orifice, the main graft having a distal orifice end which when expanded serves to receive proximal ends of a pair of expandable peripheral grafts, wherein each graft comprises an expandable stent and at least one cover over and/or in the stent, and wherein the cross-sectional area of the distal orifice when expanded is sufficiently less than the sum of the cross-sectional areas of the proximal ends of the peripheral grafts when expanded within the distal orifice so as to form a seal with the distal orifice when the pair of grafts are expanded therein.

* * * * *